United States Patent
Brennan et al.

(10) Patent No.: US 10,022,417 B2
(45) Date of Patent: Jul. 17, 2018

(54) PEPTIDES AND COMPOSITIONS THEREOF FOR IMPROVEMENT OF GLYCAEMIC MANAGEMENT IN A MAMMAL

(71) Applicants: University College Dublin, National University Of Ireland, Dublin, Dublin (IE); University of Limerick, Limerick (IE)

(72) Inventors: Lorraine Brennan, County Dublin (IE); Aisling Robinson, Dublin (IE); Nessa Noronha, County Wicklow (IE); Dick Fitzgerald, County Limerick (IE); Alice Nongonierma, Limerick (IE); Therese Holton, County Kildare (IE); Helen Roche, Dublin (IE); J C Jacquier, County Dublin (IE); Denis Shields, Dublin (IE); Eileen Gibney, County Dublin (IE)

(73) Assignees: University College Dublin, National University Of Ireland, Dublin, Dublin (IE); University of Limerick, Limerick (IE)

( * ) Notice: Subject to any disclaimer, the term of this patent is extended or adjusted under 35 U.S.C. 154(b) by 0 days.

(21) Appl. No.: 15/310,444

(22) PCT Filed: May 12, 2015

(86) PCT No.: PCT/EP2015/060522
§ 371 (c)(1),
(2) Date: Nov. 10, 2016

(87) PCT Pub. No.: WO2015/173266
PCT Pub. Date: Nov. 19, 2015

(65) Prior Publication Data
US 2017/0112890 A1   Apr. 27, 2017

(30) Foreign Application Priority Data

May 12, 2014 (EP) .................... 14167891

(51) Int. Cl.
*A61K 38/01* (2006.01)
*C07K 14/47* (2006.01)
*A61P 3/10* (2006.01)

(52) U.S. Cl.
CPC ........ *A61K 38/018* (2013.01); *C07K 14/4732* (2013.01)

(58) Field of Classification Search
CPC .......................... A61K 38/018; C07K 14/4732
See application file for complete search history.

(56) References Cited

U.S. PATENT DOCUMENTS

2005/0089969 A1   4/2005  Wissler et al.
2011/0160138 A1*  6/2011  Ohsawa ................ A61K 38/10
                                                  514/17.7

FOREIGN PATENT DOCUMENTS

| DE | 101 49 668 A1 | 4/2003 |
| EP | 2 735 616 A1 | 5/2014 |
| WO | WO 2006/026569 A2 | 3/2006 |
| WO | WO 2012/176659 A1 | 12/2012 |
| WO | WO 2015/173266 A1 | 11/2015 |

OTHER PUBLICATIONS

Hyperglycemia, from http://www.medicinenet.com/hyperglycemia/article.htm, pp. 1-7, Oct. 7, 2016.*
Insulin Resistance, from http://www.medicinenet.com/insulin_resistance/article.htm, pp. 1-11, Aug. 31, 2016.*
PCT/EP2015/060522, Notification of Transmittal of the International Preliminary Report on Patentability, dated Aug. 16, 2016, titled "Peptides and Compositions Thereof for Improvement of Glycaemic Management in a Mammal," 12 pages.
PCT/EP2015/060522, International Search Report and Written Opinion, dated Aug. 14, 2015, titled "Peptides and Compositions Thereof for Improvement of Glycaemic Management in a Mammal," 14 pages.
Database Geneseq [Online] Jun. 20, 2013 (Jun. 20, 2013), "Casein Protein Fragment, SEQ ID 3," retrieved from accession No. GSP: BAJ56683 Database accession No. BAJ56683, 1 page.
Database Geneseq [Online] Jun. 20, 2013 (Jun. 20, 2013), "Casein Protein Fragment, SEQ ID 4," retrieved from EBI accession No. GSP:BAJ56684 Database accession No. BAJ56684, 1 page.
Database Geneseq [Online] Jun. 20, 2013 (Jun. 20, 2013), "Casein Protein Fragment, SEQ ID 16," retrieved from EBI accession No. GSP: BAJ56696 Database accession No. BAJ56696, 1 page.
Database Geneseq [Online] May 4, 2006 (May 4, 2006), "Bovine Beta-Casein Peptide Fragment (aa114-169)," retrieved from EBI accession No. GSP: AEG20987 Database accession No. AEG20987, 2 pages.
Hermitte, L., et al., "Dietary Protection Against Diabetes in NOD Mice: Lack of a Major Change in the Immune System," *Diabete & Metabolisme* (Paris), 21: 261-268 (1995).
Saavedra, L., et al., "An Overview of 'Omic' Analytical Methods Applied in Bioactive Peptide Studies," *Food Research International*, 54: 925-934 (2013).
Su, R., et al., "Pancreatic Hydrolysis of Bovine Casein: Peptide Release and Time-Dependent Reaction Behavior," *Food Chemistry*, 133: 851-858 (2012).

(Continued)

*Primary Examiner* — Julie Ha
*Assistant Examiner* — Li N Komatsu
(74) *Attorney, Agent, or Firm* — Hamilton, Brooks, Smith & Reynolds, P.C.

(57) ABSTRACT

A peptide having 12 to 60 amino acids and including (a) a sequence of SEQUENCE ID NO: 11, or (b) a fragment of SEQUENCE ID NO: 11 that includes the sequence of SEQUENCE ID NO: 1 or 5, is described for use in improving glycemic management in a mammal. A composition, for example a food product, that includes substantially all of the peptides of SEQUENCE ID NO:'s 1 to 11, that is capable of reducing post-prandial blood glucose levels, and increasing insulin secretion in humans, is also described.

2 Claims, 11 Drawing Sheets

(56) References Cited

OTHER PUBLICATIONS

Turbay, M.B.E., et al., "β-Casein Hydrolysate Generated by the Cell Envelope-Associated Proteinase of *Lactobacillus delbrueckii* ssp. *lactis* CRL 581 Protects Against Trinitrobenzene Sulfonic Acid-Induced Colitis in Mice," *J Dairy Sci.*, 95: 1108-1118 (2012).
Wang, G-S., et al., "Hydrolysed Casein Diet Protects BB Rats from Developing Diabetes by Promoting Islet Neogensis," *J. Autoimmunity*, 15: 407-416 (2000).

* cited by examiner

PEPTIDES AND COMPOSITIONS THEREOF FOR IMPROVEMENT OF GLYCAEMIC MANAGEMENT IN A MAMMAL

This application is the U.S. National Stage of International Application No. PCT/EP2015/060522, filed May 12, 2015, which designates the U.S., published in English, and claims priority under 35 U.S.C. §§ 119 or 365(c) to European Application No. 14167891.2, filed May 12, 2014. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:
a) File name: 53781000002_SEQUENCELISTING.txt; created Nov. 10, 2016, 5 KB in size.

BACKGROUND TO THE INVENTION

High blood sugar levels (hyperglycaemia) are increasingly prevalent due to the spiralling levels of obesity worldwide. The WHO estimates that more than 1.4 billion adults over the age of 20 are overweight/obese, whereas one third of adults in the US and 108 million people in Asia have been diagnosed with diabetes. Hyperglycaemia is now as important as hypertension and hypercholesterolaemia, which is leading to increased awareness among health professionals and health-conscious consumers who demand products to aid post-prandial glucose levels. US2005/0089969 discloses insulin mimetic peptides.

It is an object of the invention to overcome at least one of the above-referenced problems.

STATEMENTS OF INVENTION

Broadly, the Applicants have identified a peptide, SEQUENCE ID NO: 11, and bioactive fragments thereof, that have utility in improving glycaemic management/status in mammals, in particular increasing insulin secretion following oral ingestion. The peptide of SEQUENCE ID NO: 11 has approximately 94% sequence identity with SEQUENCE ID NO: 2 of US2005/0089969 and has a number of different residues at functionally important positions. In particular, the Applicant has identified that the peptides, and a composition comprising the peptides, can increase insulin secretion in-vitro in pancreatic beta cells (FIGS. 7A-7C). The Applicant has also shown that acute treatment with a composition comprising the peptides had a glucose lowering effect during a glucose tolerance test in ob/ob mice, and caused a decrease in liver fat content in the mice (FIGS. 8 and 9). Using a diet induced obesity model, animals treated for 12 weeks with a composition comprising the peptides in the context of high fat feeding improved glucose clearance during a glucose tolerance test (GTT) compared to high fat feeding alone (FIG. 11). Additionally, the Applicant has demonstrated that a composition comprising peptides of the invention when administered to humans in a clinical study along with a carbohydrate meal causes a lowering of blood glucose levels and an increase in insulin levels (FIGS. 1 and 2).

The peptides are, or comprise, SEQUENCE ID NO: 11 below, and bioactive fragments thereof that typically include the sequence of SEQUENCE ID NO: 1 or 5, or both.

YPVEPFTESQSLTLTDVENLHLPLPLLQSWMHQPHQPLPPTVMFPPQSV LSLSQSK (SEQUENCE ID NO: 11)

Specific bioactive fragments include SEQUENCE ID NOs 1 to 10 below.

HQPHQPLPPTVMFPPQSVL (SEQUENCE ID NO: 1)

HQPHQPLPPTVMFPPQSVLSLSQSK (SEQUENCE ID NO: 2)

LQSWMHQPHQPLPPTVMFPPQSVL (SEQUENCE ID NO: 3)

LQSWMHQPHQPLPPTVMFPPQSVLSLSQSK (SEQUENCE ID NO: 4)

PPQSVLSLSQSK (SEQUENCE ID NO: 5)

MHQPHQPLPPTVMFPPQSVL (SEQUENCE ID NO: 6)

MHQPHQPLPPTVMFPPQSVLSLSQSK (SEQUENCE ID NO: 7)

SWMHQPHQPLPPTVMFPPQSVL (SEQUENCE ID NO: 8)

SWMHQPHQPLPPTVMFPPQSVLSLSQSK (SEQUENCE ID NO: 9)

YPVEPFTESQSLTLTDVENLHLPLPLLQSWMHQPHQPLPPTVMFPPQSVL (SEQUENCE ID NO: 10)

In one aspect, the invention relates to a peptide including (a) a sequence of SEQUENCE ID NO: 11, or (b) a bioactive fragment thereof, that preferably includes the sequence of SEQUENCE ID NO: 1 or 5 (hereafter "peptide of the invention").

In another aspect, the invention relates to a peptide of the invention for use in improving glycaemic management and aspects of the metabolic syndrome in a mammal.

In one embodiment, the invention relates to a peptide of the invention for use in lowering plasma blood glucose levels, especially post-prandial blood glucose levels, in a mammal.

In one embodiment, the invention relates to a peptide of the invention for use in treating or preventing hyperglycaemia (especially high fat diet or obesity-induced hyperglycaemia), in a mammal.

In one embodiment, the invention relates to a peptide of the invention for use in increasing post prandial insulin secretion in a mammal.

In one embodiment, the invention relates to a peptide of the invention for use in regulating glucose homeostasis, in a mammal.

In one embodiment, the invention relates to a peptide of the invention for use in treating or preventing or attenuating insulin resistance, in a mammal.

In one embodiment, the invention relates to a peptide of the invention for use in lowering plasma cholesterol levels, in a mammal.

In one embodiment, the invention relates to a peptide of the invention for use in treating or preventing or lowering liver fat content, in a mammal.

In one embodiment, the invention relates to a peptide of the invention for use in promoting an anti-inflammatory response in a mammal.

In one embodiment, the invention relates to a peptide of the invention for use in reducing high fat diet or obesity induced inflammation.

In one embodiment, the invention relates to a peptide of the invention for use in a method for the treatment or prevention of an inflammatory disorder in a mammal.

In one embodiment, the invention relates to a peptide of the invention for use in lowering plasma blood glucose levels, especially post-prandial blood glucose levels, and increasing insulin secretion, especially post-prandial insulin secretion, in a mammal.

In another aspect, the invention also relates to a composition comprising a plurality of different peptides of the invention, for example at least 2, 3, 4, 5, 6, 7, 8, 9, 10 or 11 different peptides of the invention. Preferably, each peptide of the invention includes a sequence of SEQUENCE ID NO: 11, or a fragment thereof that include the sequence of SEQUENCE ID NO: 1 or 5.

In a further aspect, the invention also relates to a composition comprising substantially all of peptides of SEQUENCE ID NO's: 1 or 11. Suitably, the composition is a hydrolysate of a bovine casein product. The composition may be a pharmaceutical, food product, food supplement, dietary supplement, speciality food (for diabetics or infants or geriatric patients).

In another aspect, the invention relates to a composition of the invention for use in improving glycaemic management in a mammal.

In one embodiment, the invention relates to a composition of the invention for use in lowering plasma blood glucose levels, especially post-prandial blood glucose levels, in a mammal.

In one embodiment, the invention relates to a composition of the invention for use in treating or preventing hyperglycaemia (especially high fat diet or obesity-induced hyperglycaemia), in a mammal.

In one embodiment, the invention relates to a composition of the invention for use in increasing post prandial insulin secretion in a mammal.

In one embodiment, the invention relates to a composition of the invention for use in regulating glucose homeostasis, in a mammal.

In one embodiment, the invention relates to a composition of the invention for use in treating or preventing or attenuating insulin resistance, in a mammal.

In one embodiment, the invention relates to a composition of the invention for use in lowering plasma cholesterol levels, in a mammal.

In one embodiment, the invention relates to a composition of the invention for use in treating or preventing or lowering liver fat content, in a mammal.

In one embodiment, the invention relates to a composition of the invention for use in promoting an anti-inflammatory response in a mammal.

In one embodiment, the invention relates to a composition of the invention for use in reducing high fat diet or obesity induced inflammation.

In a further aspect, the invention relates to a food product comprising a composition of the invention. Typically, the food product is a Food for Specific Medicinal Purposes (FSMP). In one embodiment, the food product is a diary product. I In another aspect, the invention relates to a food product of the invention for use in improving glycaemic management in a mammal.

In one embodiment, the invention relates to a food product of the invention for use in treating or preventing hyperglycaemia (especially high fat diet or obesity-induced hyperglycaemia), in a mammal.

In one embodiment, the invention relates to a food product of the invention for use in increasing post prandial insulin secretion in a mammal.

In one embodiment, the invention relates to a food product of the invention for use in regulating glucose homeostasis, in a mammal.

In one embodiment, the invention relates to a food product of the invention for use in treating or preventing or attenuating insulin resistance, in a mammal.

In one embodiment, the invention relates to a food product of the invention for use in lowering plasma cholesterol levels, in a mammal.

In one embodiment, the invention relates to a food product of the invention for use in treating or preventing or lowering liver fat content, in a mammal.

In one embodiment, the invention relates to a food product of the invention for use in promoting an anti-inflammatory response in a mammal.

In one embodiment, the invention relates to a food product of the invention for use in reducing high fat diet or obesity induced inflammation.

In a further aspect, the invention relates to a composition or peptide of the invention for use in preventing or treating a condition selected from a metabolic disorder or obesity. Thus, the invention also relates to a method for the prevention or treatment of a metabolic disorder in a human, comprising the step of administering to the human a therapeutically effective amount of the composition or peptide of the invention.

In a further aspect, the invention provides a pharmaceutical composition comprising a peptide or composition of the invention in combination with a suitable pharmaceutical carrier.

The invention provides a bovine casein product derived hydrolysate comprising a plurality of different peptides of the invention, for example at least 2, 3, 4, 5, 6, 7, 8, 9, 10 or 11 different peptides of the invention. Suitably, at least 1%, 10%, 20%, 30%, 40%, 50%, 60%, 70%, 80% or 90% (w/w) of the hydrolysate comprises peptides of the invention. Typically, the hydrolysate of the invention is obtained by performing hydrolysis on a bovine casein product using a gastro-intestinal enzyme preparation at the temperature range of 30° C. to 60° C.

The composition of the invention may comprise a hydrolysate of the invention.

The invention also relates to a method of making a bovine casein product derived hydrolysate of the invention comprising the steps of providing a bovine casein derived product, performing enzymatic hydrolysis on the bovine casein derived product using a gastrointestinal protease preparation at a temperature of 30° C. to 60° C. for a suitable period of time.

The bovine-casein product typically comprises a casein salt, examples of which will be well known to those skilled in the art and include sodium caseinate. Typically, the bovine casein product (and/or the casein hydrolysate) is substantially free (i.e. less than 5%, 4%, 3%, 2%, 1%, 0.5%, 0.2%, 0.1% (w/w) of other milk proteins, for example whey proteins.

Typically, the ratio of protease to casein substrate (w.w) is from 0.1 to 1.0%, preferably 0.2 to 2.0%.

Suitably, hydrolysis of the casein substrate with protease preparation is carried out at a temperature of from 30° C. to 60° C.

Definitions

In this specification, the term "improving glycaemic management" should be understood to mean one or more of treating or preventing hyperglycaemia, increasing post prandial insulin secretion, regulating glucose homeostasis, reducing insulin resistance, increasing levels of glucagon-like-peptide, reducing hepatic fat content, protecting against HFD or obesity-induced inflammation. The term "improving metabolic health" should be understood to mean lowering plasma cholesterol levels, lowering liver fat content, or promoting an anti-inflammatory response- or any combination thereof.

In this specification, the term "mammal" should be understood to mean a higher mammal, especially a human. Typically, the human has a disorder selected from a metabolic disorder such as diabetes, or obesity.

The term "peptide" used herein refers to a polymer composed of up to 60 amino acid monomers via peptide bond linkage. Peptides (including variants and fragments thereof) of and for use in the invention may be generated wholly or partly by chemical synthesis or by expression from nucleic acid. For example, the peptides of and for use in the present invention can be readily prepared according to well-established, standard liquid or, preferably, solid-phase peptide synthesis methods known in the art (see, for example, J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984). When necessary, any of the peptides employed in the invention can be chemically modified to increase their stability. A chemically modified peptide or a peptide analog includes any functional chemical equivalent of the peptide characterized by its increased stability and/or efficacy in vivo or in vitro in respect of the practice of the invention. The term peptide analog also refers to any amino acid derivative of a peptide as described herein. A peptide analog can be produced by procedures that include, but are not limited to, modifications to side chains, incorporation of unnatural amino acids and/or their derivatives during peptide synthesis and the use of cross-linkers and other methods that impose conformational constraint on the peptides or their analogs. Examples of side chain modifications include modification of amino groups, such as by reductive alkylation by reaction with an aldehyde followed by reduction with NaBH$_4$; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with NABH$_4$. The guanidino group of arginine residues may be modified by the formation of heterocyclic condensation products with reagents such as 2,3-butanedione, phenylglyoxal and glyoxal. The carboxyl group may be modified by carbodiimide activation via o-acylisourea formation followed by subsequent derivatization, for example, to a corresponding amide. Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH. Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. Peptide structure modification includes the generation of retro-inverso peptides comprising the reversed sequence encoded by D-amino acids.

In this specification, the term "peptide of the invention" means a peptide including a sequence of SEQUENCE ID NO: 11, or a bioactive fragment thereof, or a bioactive variant of either. The term "bioactive fragment thereof" as applied to SEQUENCE ID NO: 11, means a fragment of SEQUENCE ID NO: 11 having at least 10 amino acids and which is capable of increasing insulin secretion from pancreatic beta cells compared with a control in the in-vitro test described below with reference to FIG. 7B. Disclosed examples of bioactive fragments of SEQUENCE ID NO: 11 have at least 12 amino acids and include the sequence PPQSVLSLSQSK (SEQUENCE ID NO: 5) or the sequence HQPHQPLPPTVMFPPQSVL (SEQUENCE ID NO: 1). Specific examples of bioactive fragments of SEQUENCE ID NO: 11 include the sequence of SEQUENCE ID NO'S 1 to 11 (FIG. 7B). The term "bioactive variant" as applied to a given reference peptide means a variant of the peptide having at least 80% sequence homology and typically at least 90%, preferably at least 95%, and ideally at least 96%, 97% 98% or 99% sequence homology across the full length of the peptide and which is capable of increasing insulin secretion from pancreatic beta cells compared with a control in the in-vitro test described below with reference to FIG. 7B. In this context, sequence homology comprises both sequence identity and similarity, i.e. a variant that shares 90% amino acid homology with SEQUENCE ID NO: 11 is one in which any 90% of aligned residues across the full length of the variant sequence are either identical to, or conservative substitutions of, the corresponding residues in SEQUENCE ID NO: 11.

The compositions of the invention comprises a mixture of different peptides comprising at least 2 peptides, for example 2, 3, 4, 5, 6, 7, 8, 9, 10 or 11 different peptides, in which the peptides are selected from SEQUENCE ID NO: 11 or a bioactive fragment thereof. In one embodiment, the composition comprises substantially all of the peptides of SEQUENCE ID NO: 1 to 11, for example 8, 9 or 10 of the peptides. The term "composition comprising substantially all of peptides of SEQUENCE ID NO'S 1 to 11" should be understood to mean a composition comprising at least 8, 9 or 10 of the peptides. The composition may also include additional peptides, polypeptides or proteins, or other components, for example a poorly digestible carbohydrate.

The composition may be prepared by hydrolysing a bovine casein product, for example sodium caseinate, using a gastrointestinal protease preparation at a suitable temperature and for a sufficient period of time to provide a hydrolysate comprising at least two of the peptides of SEQUENCE ID NO: 1 to 11. The term "bovine casein product" as used herein should be understood to mean products derived from bovine milk that are predominantly composed on casein protein, for example rennet caseinsates and acid caseinates (sodium, calcium and potassium caseinates). The term "gastrointestinal protease preparation" as employed herein should be understood to mean a protease preparation that includes trypsin, chymotrypsin, and elastase. Typically, the hydrolysis is carried out at 30° C.-60° C.

In one embodiment, the composition of the invention is a casein-derived hydrolysate comprising a range of peptides of SEQUENCE ID NO's: 1 to 11, hereafter referred to as "LFC24". The composition of the invention is typically capable of lowering post-prandial blood glucose levels, increasing post-prandial insulin secretion levels, or both, when administered to an adult human according to the conditions of the clinical study described below.

The invention also relates to a composition comprising one or more peptides of the invention. The term "composition" may refer to a food product, a pharmaceutical product, a dietary supplement or nutritional supplement. The food product may be a solid food or liquid. Examples of food products include dairy products (such as milk drinks, yoghurts, yoghurt drinks, cheeses, spreads), beverages, bakery products, meat products, breakfast cereals, snack food products. The dietary supplement may be provided in any form, including as a powder, granules, flakes or in a unit dose form such as a sachet of powder, pill, capsule, tablet, losange or the like.

The invention also relates to a comestible product, for example a food product comprising a composition of the invention. The food product may be a solid food or liquid. Examples of food products include dairy products (such as milk drinks, yoghurts, yoghurt drinks, cheeses, spreads), beverages, bakery products, meat products, breakfast cereals, snack food products. The food product may comprise any amount of the composition of the invention, for example from 0.1% to 30% (w/w).

The food product may be a Food for Specific Medicinal Purposes (FSMP) which is defined as foods that are specifically formulated, processed and intended for the dietary management of diseases, disorders or medical conditions of individuals who are being treated under medical supervision. These foods are intended for the exclusive or partial feeding of people whose nutritional requirements cannot be met by normal foods.

"Inflammatory disorder" means an immune-mediated inflammatory condition that affects humans and is generally characterised by dysregulated expression of one or more cytokines. Examples of inflammatory disorders include skin inflammatory disorders, inflammatory disorders of the joints, inflammatory disorders of the cardiovascular system, certain autoimmune diseases, lung and airway inflammatory disorders, intestinal inflammatory disorders. Examples of skin inflammatory disorders include dermatitis, for example atopic dermatitis and contact dermatitis, acne vulgaris, and psoriasis. Examples of inflammatory disorders of the joints include rheumatoid arthritis. Examples of inflammatory disorders of the cardiovascular system are cardiovascular disease and atherosclerosis. Examples of autoimmune diseases include Type 1 diabetes, Graves disease, Guillain-Barre disease, Lupus, Psoriatic arthritis, and Ulcerative colitis. Examples of lung and airway inflammatory disorders include asthma, cystic fibrosis, COPD, emphysema, and acute respiratory distress syndrome. Examples of intestinal inflammatory disorders include colitis and inflammatory bowel disease. Other inflammatory disorders include cancer, hay fever, periodontitis, allergies, hypersensitivity, ischemia, depression, systemic diseases, post infection inflammation and bronchitis.

In this specification, the term "Metabolic disorder" should be understood to include pre-diabetes, diabetes; Type-1 diabetes; Type-2 diabetes; metabolic syndrome; obesity; diabetic dyslipidemia; hyperlipidemia; hypertension; hypertriglyceridemia; hyperfattyacidemia; hypercholerterolemia; hyperinsulinemia, MODY, and HNF1A-MODY.

The invention also provides a pharmaceutical composition comprising a peptide or composition of the invention in combination with a suitable pharmaceutical excipient. The term "excipient" refers to a diluent, adjuvant, excipient, or vehicle with which the peptide(s) or composition is administered. Such pharmaceutical excipients can be sterile liquids, such as water and oils, including those of petroleum, animal, vegetable or synthetic origin, such as peanut oil, soybean oil, mineral oil, sesame oil and the like. Water is a preferred excipient when the pharmaceutical composition is administered intravenously. Saline solutions and aqueous dextrose and glycerol solutions can also be employed as liquid excipients, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like.

**p<0.01. Cells are exposed to (1) 16.7 mM glucose (2) 16.7 mM glucose and 10 mM ala and (3) 16.7 mM glucose and LFC24 (1 mg/ml).

Figure 6:
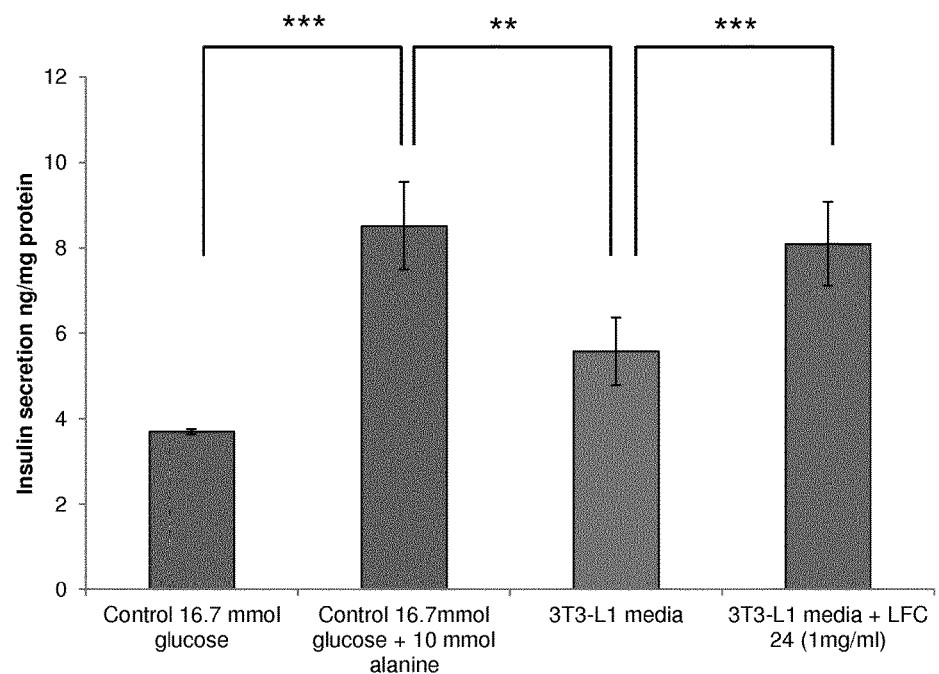

FIG. 6. Insulin secretion from pancreatic beta cells (BRIN-BD11). Insulin secretion from BRIN-BD11 cells following 2 hour incubation with 3T3-L1 adipocyte conditioned media and 3T3-L1 media with LFC24 (n=4). Values are means±SD. Exposure to LFC 24 prevented pancreatic beta cell dysfunction. p<0.01, *p<0.001

Figure 7A:
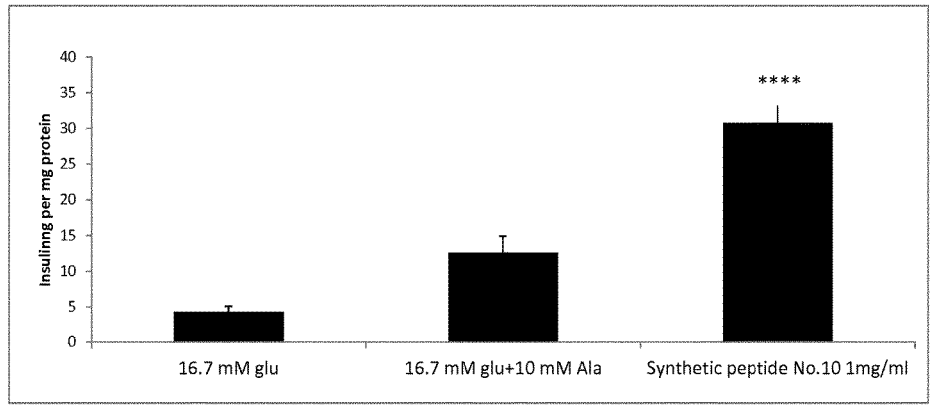

FIG. 7A. Insulin secretion from pancreatic beta cells (BRIN BD11) (n=3/4) following exposure to 16.7 mmol/l glucose and the synthetic peptide No. 10. Values are means±SD. Positive controls are 16.7 mM glucose and 16.7 mM glucose plus 10 mM alanine. ****p<0.0001

Figure 7B:
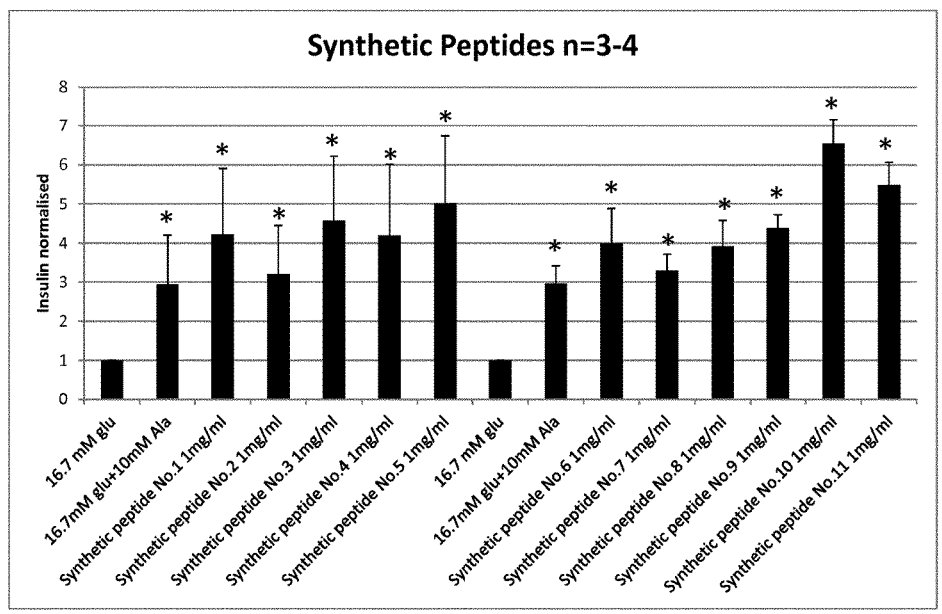

FIG. 7B. Insulin secretion from pancreatic beta cells (BRIN BD11) (n=3/4) induced following exposure to 16.7 mmol/l glucose and the synthetic peptides. Values are means±SD. Positive controls are 16.7 mM glucose and 16.7 mM glucose plus 10 mM alanine. *P<0.05 compared to glucose control.

Figure 7C:
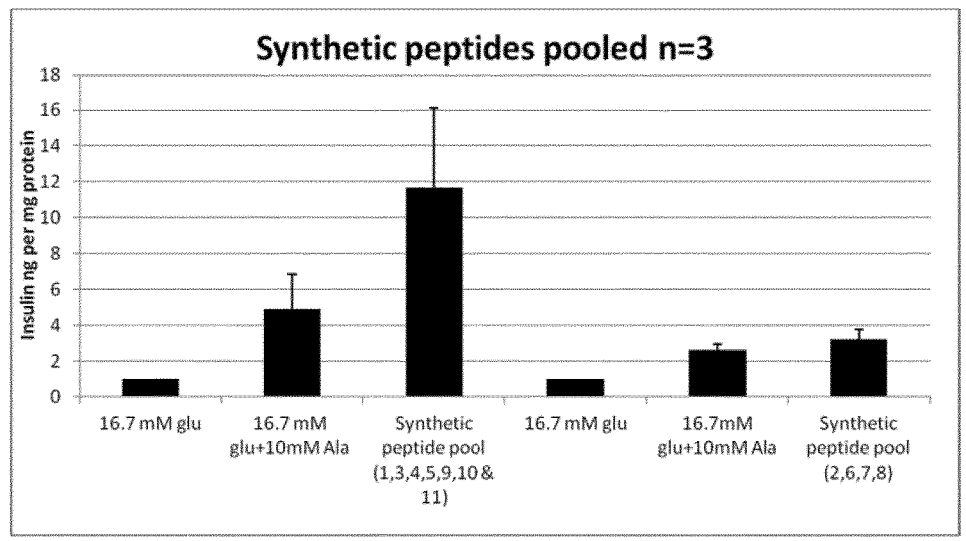

FIG. 7C. Insulin secretion from pancreatic beta cells (BRIN BD11) (n=3) following exposure to 16.7 mmol/l glucose and combination of the synthetic peptides. Positive controls are 16.7 mM glucose and 16.7 mM glucose and 10 mM alanine. A pooled sample of peptides 1, 3, 4, 5, 9, 10 and 11 was more potent than the combination of synthetic peptides 2, 6, 7 and 8.

Figure 8:
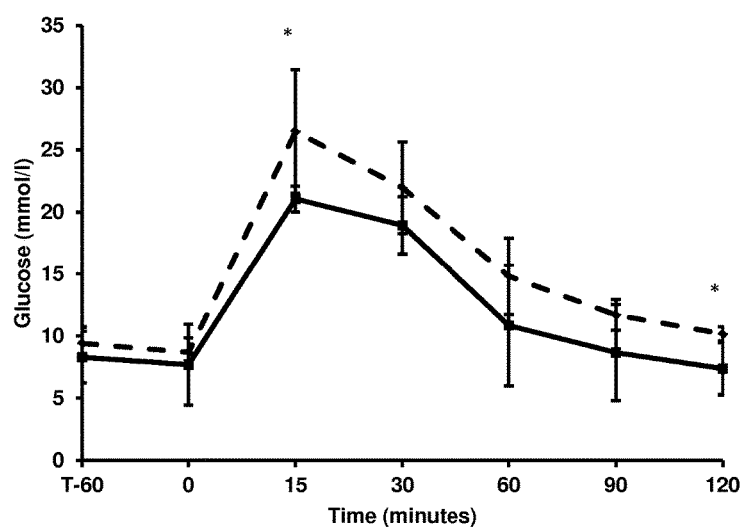

FIG. 8. Acute treatment with LFC 24 had a glucose lowering effect during a glucose tolerance test in ob/ob mice 15 minutes (*p<0.05) and 120 minutes (*p<0.05) compared to the control treatment group. Results are expressed as ±S.D. (Control n=5, treated n=6). Dashed line represents control group and solid line represent treatment with LFC24.

Figure 9:
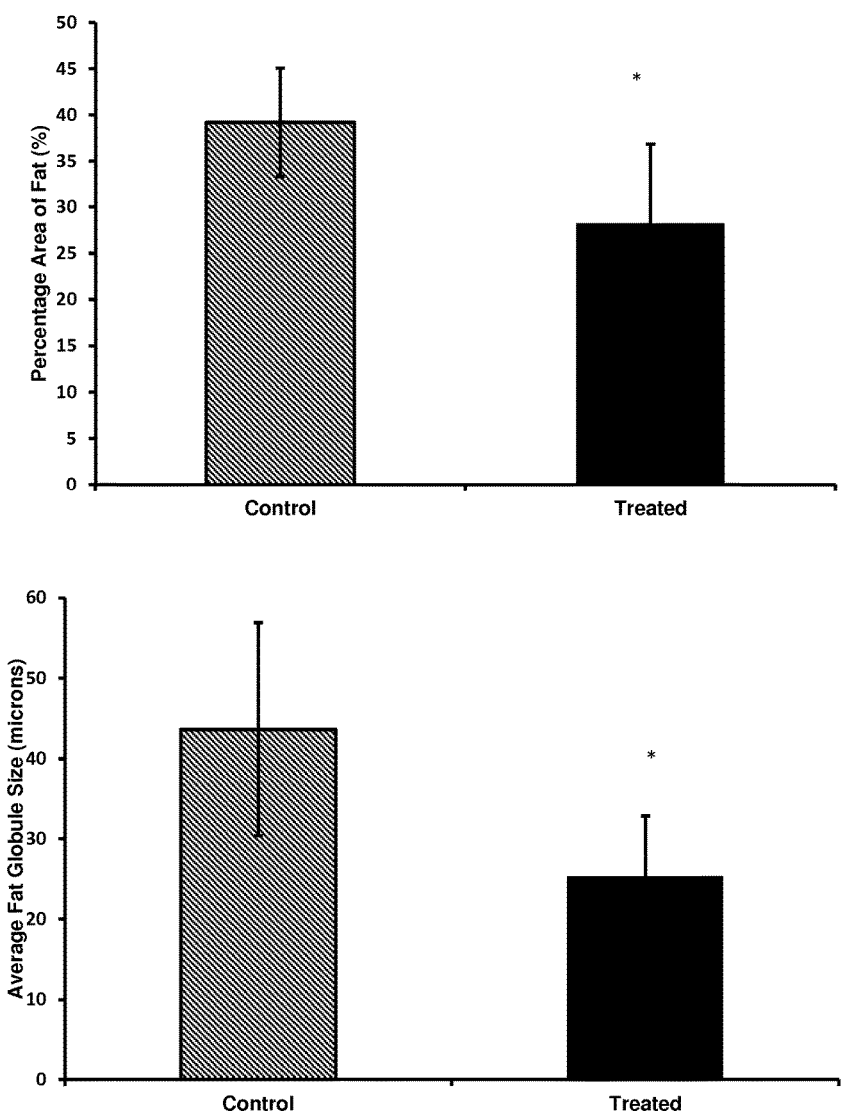

FIG. 9. Long term treatment with LFC 24 induced a significant reduction in the overall hepatic fat percentage in ob/ob mice following 12 weeks treatment. Control represents control treated mice and treated represent treatment with LFC24. Treatment with a casein-derived hydrolysate caused a 43% reduction in liver fat compared to the livers of control mice. Results are expressed as ±S.D of 6 separate 40× images of each liver. (Control n=6, LFC24 treated n=5), (p<0.05). Long term treatment with LFC 24 caused a significant reduction in the average hepatic fat globule size in ob/ob mice following 12 weeks treatment. Average fat globule size was reduced from an average of 39 microns in control livers to 28 microns in treated livers. Results are expressed as means±S.D of 6 separate 40× images of each liver. (Control n=6, LFC24 treated n=5), (*p<0.05).

Figure 10:
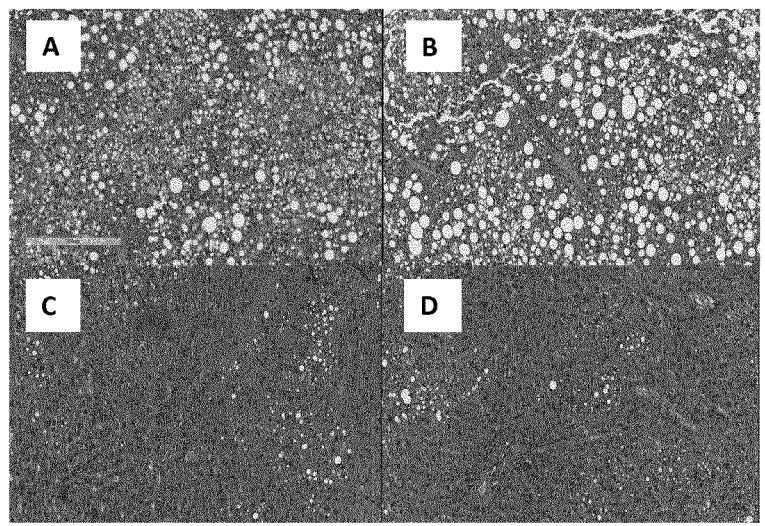

FIG. 10. Long term treatment with a casein-derived hydrolysate caused a significant reduction in the hepatic fat globule size and overall hepatic fat content in ob/ob mice following 12 weeks treatment. A & B represent H&E stained liver sections from control ob/ob mice which received water for 12 weeks. C & D represent H&E stained liver sections from ob/ob mice treated with a LFC24. Scale=300 μm FIG. 11. Glucose levels during a GTT. Values are means±SEM. LFC24 protects against high fat diet (HFD) induced glucose intolerance. Supplementation with LFC24 protected mice from HFD-induced glucose intolerance. The glycaemic response to the GTT was significantly lower in HFD+LFC24 fed mice, compared to HFD fed mice with significantly lower plasma glucose levels post glucose challenge (p<0.001, p<0.05). Also the GTT area under the curve (AUC) was significantly lower in HFD+LFC24 compared to HFD fed mice. This improvement of glycaemic control was independent of body weight as both HFDs caused equivalent weight gain.

Figures 12A, 12B:
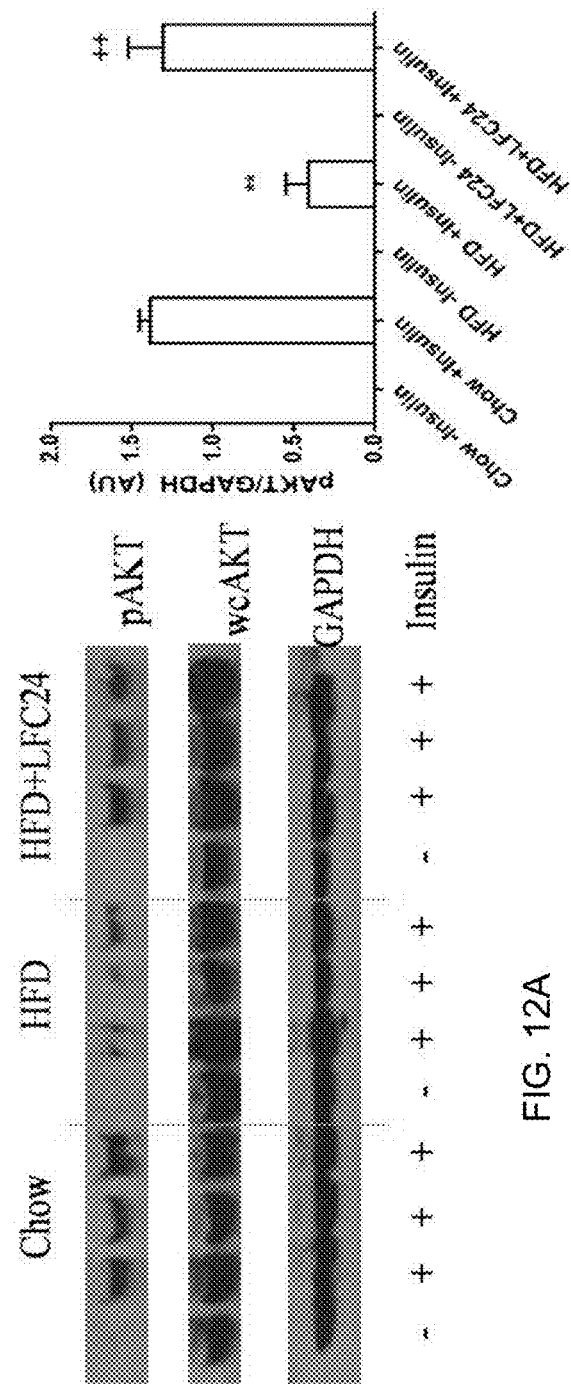

FIGS. 12A-12B. LFC24 protects against high fat diet (HFD) induced reduction of pAKT levels in adipose tissue. Mice were injected with 1.5 U/kg insulin 15 mins prior to sacrificing. Adipose tissue was immediately snap-frozen. (A) Levels of phosphorylated AKT were determined by western blot analysis. (B) Densitometry analysis of pAKT levels were normalized to GAPDH and expressed as arbitrary units (AU). (**p<0.01 w.r.t Chow+Insulin; ++p<0.01 w.r.t HFD+Insulin) (n=10 mouse/group).

Figure 13A:
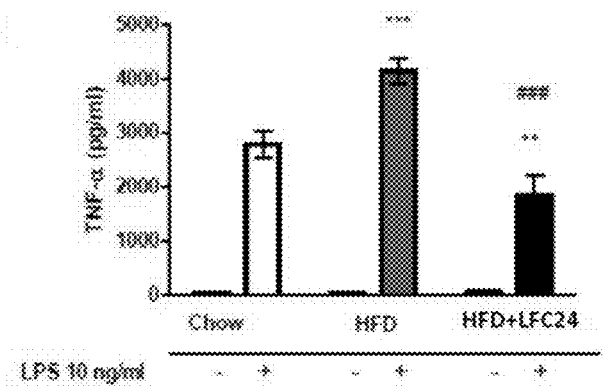
Figure 13B:
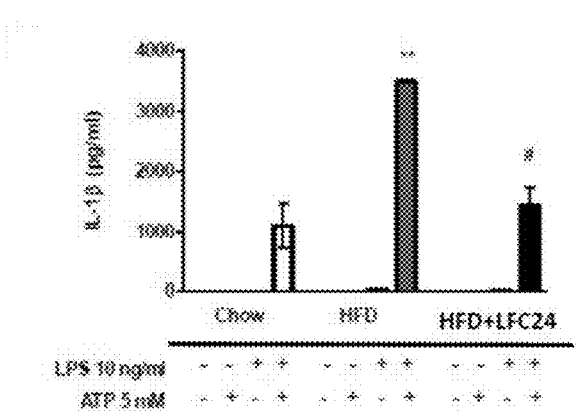
Figure 13C:
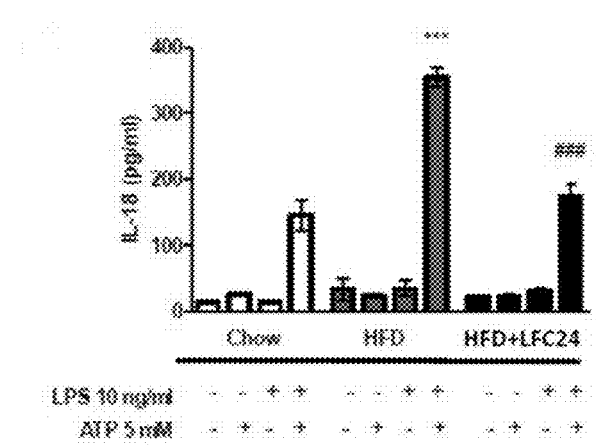

FIGS. 13A-13C. LFC24 protects against high fat diet (HFD) induced inflammation, with reduced TNF-α (FIG. 13A), IL-1β (FIG. 13B) and IL-18 (FIG. 13C) secretion from bone marrow macrophages (BMM) derived from C57Bl/6 mice fed HDF with LFC24 versus without LFC24. BMM were harvested from male C57Bl/6 mice from each study group. BMMs were cultured for 7d, seeded at a density of $1\times10^5$ cells/ml stimulated with LPS (10 ng/ml) for 3-24 h±ATP (5 mM). Supernatants were collected and TNF-α, IL-1β and IL-18 concentrations determined by ELISA (*p<0.001; p<0.01 w.r.t Chow+LPS; ####p<0.001; ###p<0.01; #p<0.05 HFD+LFC24+LPS/ATP versus HFD (no LFC24)+LPS/ATP) (n=3 mouse/group).

Figure 14A:
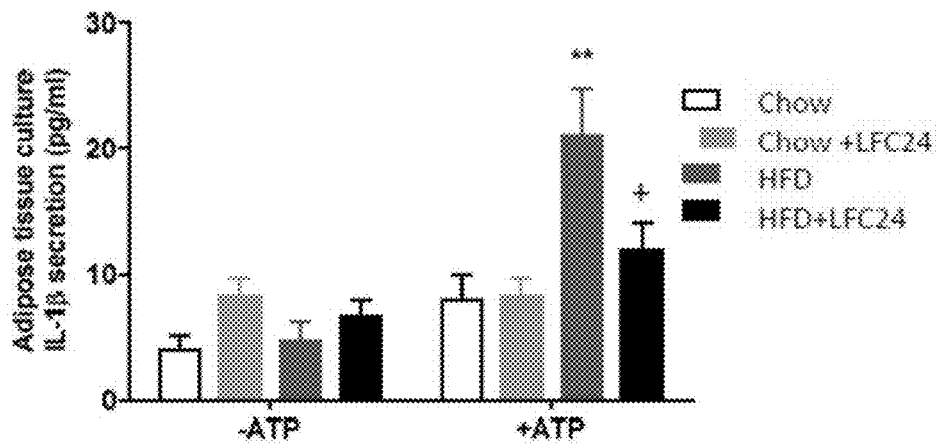
Figure 14B:
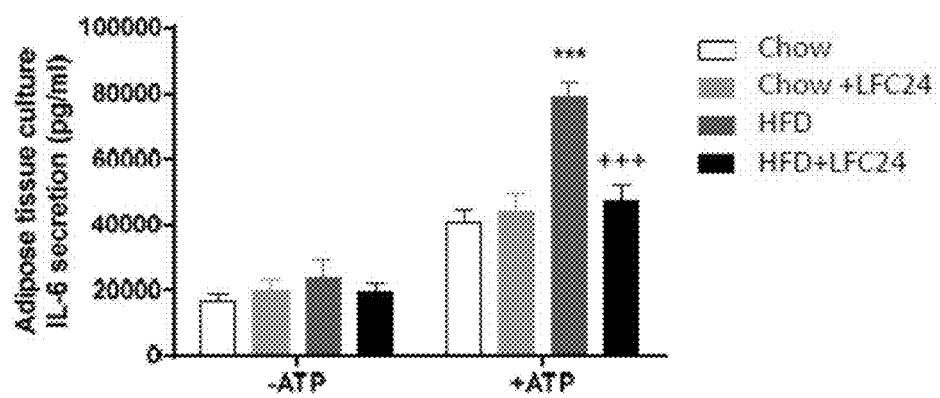
Figure 14C:
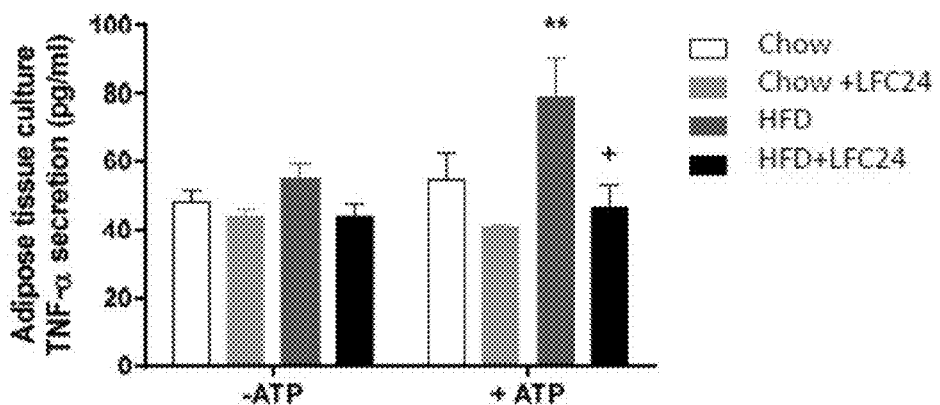

FIGS. 14A-14C. LFC24 improved adipose tissue inflammation, with reduced IL-1β IL-6 and TNF-α, secretion from adipose tissue explants derived from C57Bl/6 mice fed HDF with LFC24. Epididymal adipose tissue was harvested from mice fed either a chow diet or a HFD supplemented ±LFC24 treated water. The tissue was cultured with media ±ATP (5 mM) for 24 h. Media was harvested and profiled for IL-1β (A) IL-6 (B) and TNF-α (C) cytokine secretion (**p<0.01 w.r.t Chow+ATP; +p<0.05 w.r.t HFD+ATP) (n=9-10 mice/group).

Figure 15:
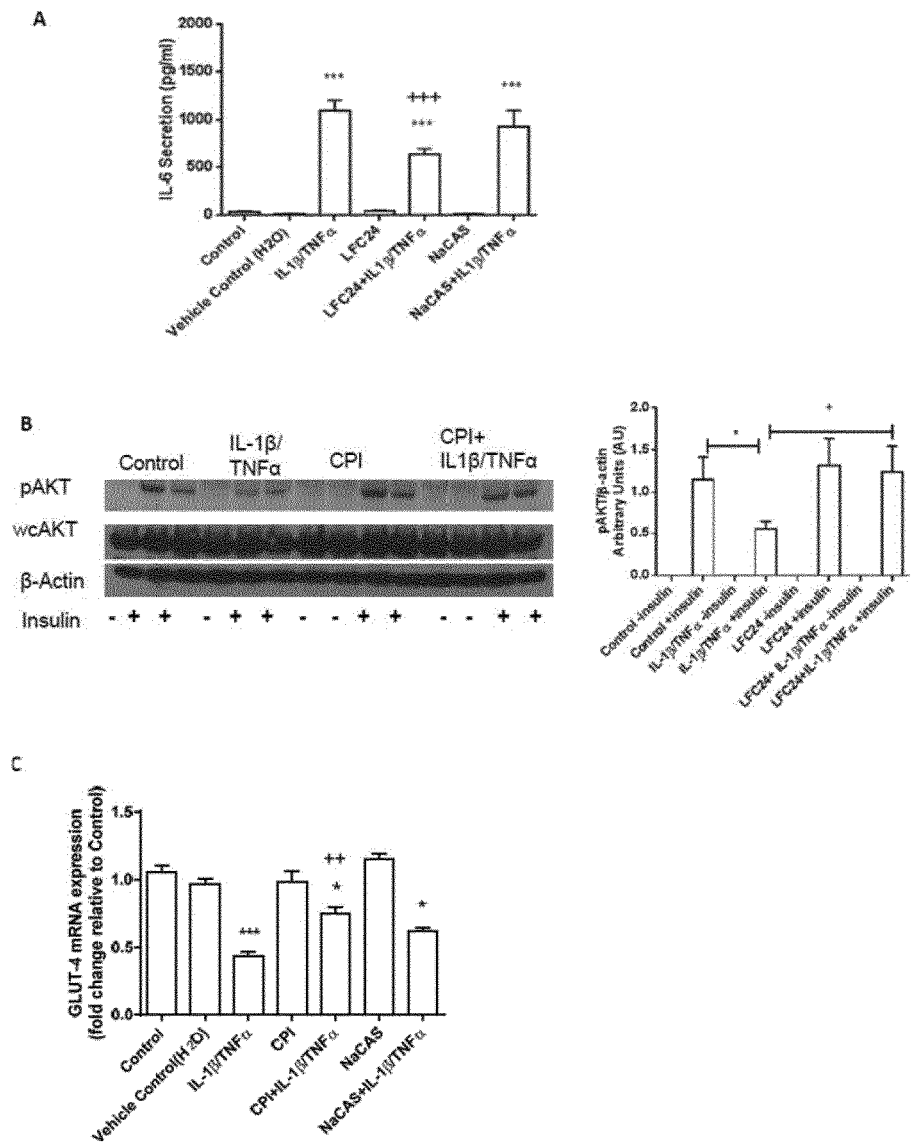

FIG. 15. LFC24 specifically inhibits the pro-inflammatory effect of IL-1 and TNF-α on IL-6 expression in 3T3-L1 adipocytes; coincident with improved insulin signalling markers pAKT and GLUT4. 3T3-L1 adipocytes were pre-treated±LFC24 (1 mg/mL) and NaCAS (1 mg/mL) for 72 h followed by a 24 h treatment with IL1β/TNFα (0.5 ng/mL+ 0.5 ng/mL). Media and cells were harvested for analysis. (A) IL-6 cytokine levels were determined by ELISA (*p<0.001 w.r.t. Control; ++p<0.01 w.r.t IL1β/TNFα). (B) phosphorylated AKT were determined by western blot analysis in 3T3-L1 cells treated±insulin (100 nM) for 15 min. (C) GLUT-4 mRNA expression was determined by RT-qPCR (*p<0.001 w.r.t. Control; **p<0.01 w.r.t Control; ++p<0.01 IL-1β/TNFα w.r.t LFC24+IL-1β/TNFα)

DETAILED DESCRIPTION OF THE INVENTION

Preparation of Bovine Casein-Derived Enzymatic Hydrolysate (LFC24)

The casein fraction of bovine milk was subjected to proteolytic digestion with a gastro-intestinal protease enzyme preparation (trypsin, chymotrypsin and elastase) between the temperature range of 30° C.-60° C. Upon completion of the reaction, the solution was heated to inactivate the enzyme, and the digest was evaporated and spray dried. The resulting powdered preparation was assayed for biological activity as described below and separated by reverse-phase solid-phase extraction (SPE) for peptide analysis.

Human Study

Study Population

Healthy subjects were recruited in the Dublin region by poster and radio advertising. The study was approved by the University College Dublin Human Ethics Research Committee. Interested candidates were screened and, once accepted, provided written, informed consent for their participation. Inclusion criteria stated that subject were aged 40-65 years, with BMI>25 kg/m² and be free from disease, prescribed medication, pregnancy or lactation.

TABLE 1

Baseline characteristics of the study population (data shown represents mean and standard deviation (SD) of 62 subjects (32 f, 30 m)

|  | Mean | SD |
| --- | --- | --- |
| Age (years) | 53.6 | 6.5 |
| BMI (kg/m$^2$) | 31.3 | 4.6 |
| Body Fat % | 37.0 | 8.2 |
| Waist Circumference(cm) | 93.7 | 10.6 |
| Systolic Blood Pressure (mmHg) | 128.9 | 16.9 |
| Diastolic Blood Pressure (mmHg) | 82.3 | 8.3 |

Study Design and Intervention

The study was a randomised crossover design with ingestion of an intact sodium caseinate and a casein-derived hydrolysate comprising all of the peptides of SEQUENCE ID NO'S: 1 to 11 (hereafter "LFC24"). In-tact sodium caseinate was obtained from Kerry Ingredients plc. Each protein beverage was prepared by reconstituting 12 g dried LFC24 or intact sodium caseinate in 120 ml mineral water (Ballygowan), giving a 10% w/v solution.

On arrival fasting subjects were instructed to consume the meal containing 75 g carbohydrate and protein beverage within ten minutes. Blood samples were taken at time points t=0, 15, 30, 60, 90 and 120 minutes.

Statistics

Data were expressed as mean values±SEM. A linear mixed model analysis was performed using SPSS 18.0 (SPSS Inc., Chicago, Ill., USA) comparing response of the control and treatment groups for all analytes. A p-value of 0.05 or less was considered significant.

Results

Figure 1:
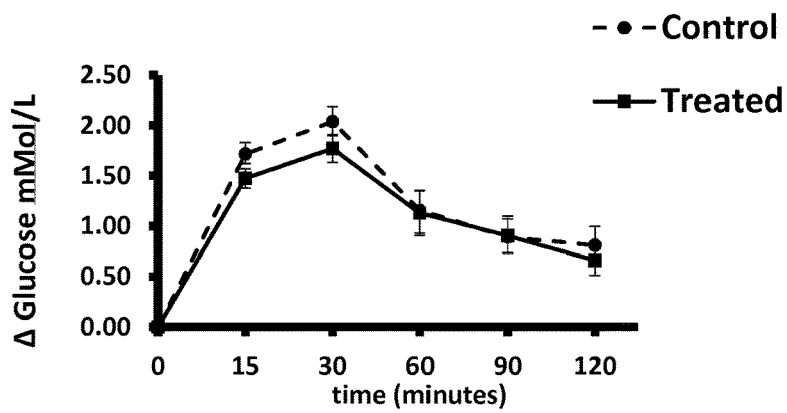
FIG. 1. Mean change in glucose (delta change, mmol/L) over 120 minutes post treatment with sodium caseinate or LFC 24. Data presented based on n=62 healthy adults where error bars represent standard error of the mean (SEM). Treatment effect significant: $p<0.05$.
Figure 2:
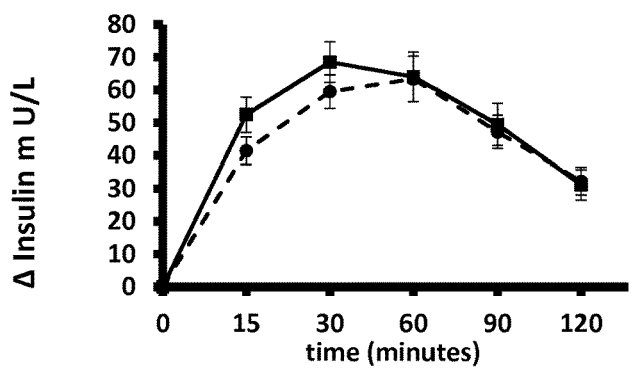
FIG. 2. Mean change in insulin (delta change, mU/L) over 120 minutes post treatment with sodium caseinate or LFC 24. Data presented based on n=62 healthy adults where error bars represent standard error of the mean (SEM). Treatment effect significant: $p<0.05$.
Figure 3:
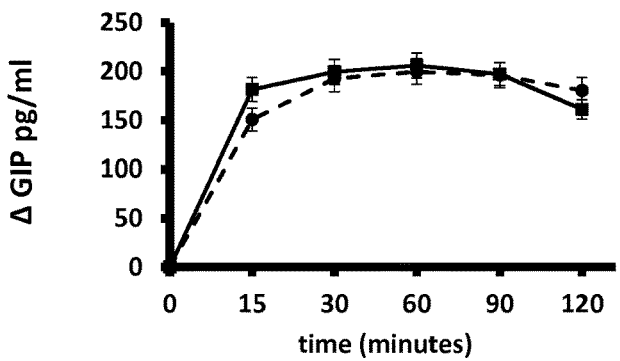
FIG. 3. Mean change in GIP (delta change, pg/ml) over 120 minutes post treatment with sodium caseinate or hydrolysed casein (LFC 24). Treatment effect significant: ns Data presented based on n=62 healthy adults where error bars represent standard error of the mean. There was a significant increase in GIP (glucagon-like peptide) whereby treatment with LFC24 caused concentrations to rise 17.1% above the control levels at the 15 minute time point for example, which was an increase of 25.95 pg/ml.
Figure 4:
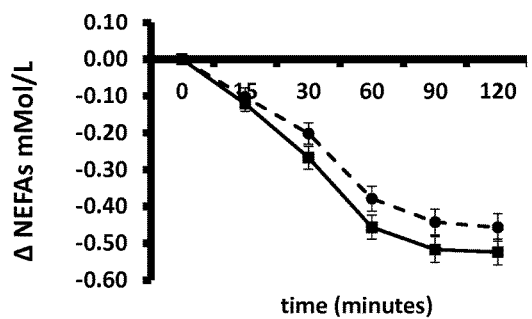
FIG. 4. Mean change in Non-Esterified Fatty Acids (delta change, mMol/L) over 120 minutes post treatment with sodium caseinate or LFC 24. Data presented based on n=62 healthy adults where error bars represent standard error of the mean. Treatment effect significant: $p<0.001$. Non-esterified fatty acids (NEFAs) were significantly reduced in response to consumption of LFC 24 compared to the intact sodium caseinate.

A total of 30 males and 32 females successfully completed the study (Table 1). The glucose and insulin response were significantly different between the LFC24 and sodium caseinate groups (FIG. 1 and FIG. 2).

In Vitro Study

Figure 5:
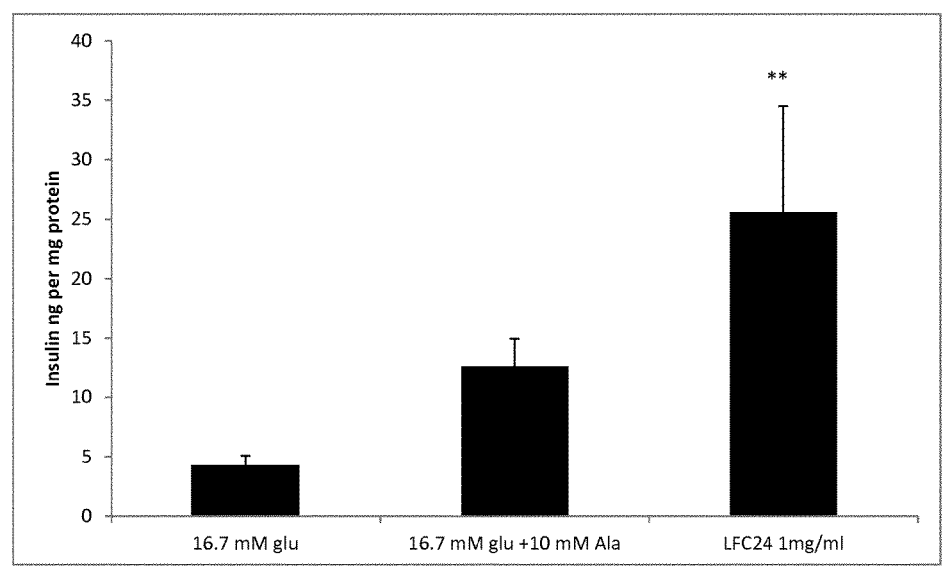
FIG. 5. Insulin secretion from BRIN BD11 cells following exposure to LFC24 (n=3/4). Values are means±SD.

LFC24 can promote insulin secretion from pancreatic beta cells (FIG. 5). Experiments were initially performed in a cell line and confirmed using primary islets (data not shown). The ability of LFC24 to rescue pancreatic beta cell function was examined using an adipocyte condition media-beta cell function model. Exposure to LFC24 rescued the beta cell insulin secretion ability (FIG. 6).

A series of peptides were identified to be present in LFC24. Following identification of the peptides a series of synthetic peptides were synthesised. The ability to promote insulin secretion was tested and the results are shown in FIG. 7.

Animal Model Study

Three animal studies were performed. Study 1 and 2 used the ob/ob mouse model and study 3 used a diet induced obesity mouse model.

Study 1 and 2

Acute Effect of a Casein-Derived Hydrolysate (LFC24) on Glucose and Insulin Levels During a Glucose Tolerance Test To assess the acute effects of LFC 24 a GTT was performed in ob/ob and C57BL/6 wildtype mice. A glucose lowering effect was found in ob/ob mice, decreased levels of glucose was observed at 15 minutes (*p<0.05) and 120 minutes (*p<0.05) compared to the control ob/ob group (FIG. 8). Insulin was measured during the GTT for ob/ob mice; treatment with the casein-derived hydrolysate one hour prior to the GTT had no effect on insulin levels at 0, 15 and 60 minutes compared to control conditions.

Effect of Supplementation with a Casein-Derived Hydrolysate (LFC24) on Liver Fat Hepatic histological studies demonstrated that treatment with a casein-derived hydrolysate (LFC24) caused a significant (p<0.05) reduction in overall fat content in the liver with a significant (p<0.05) reduction in fat droplet size (FIG. 9). Treatment with a casein-derived hydrolysate caused a 43% reduction in overall liver fat and a 28% reduction in the average fat globule size (FIG. 9) compared to the livers of control mice. Visual observation of H&E stained images of liver reveal vivid changes in liver fat following treatment (FIG. 10).

Study 3

Glycaemic Control and Insulin Signalling

Figure 11:
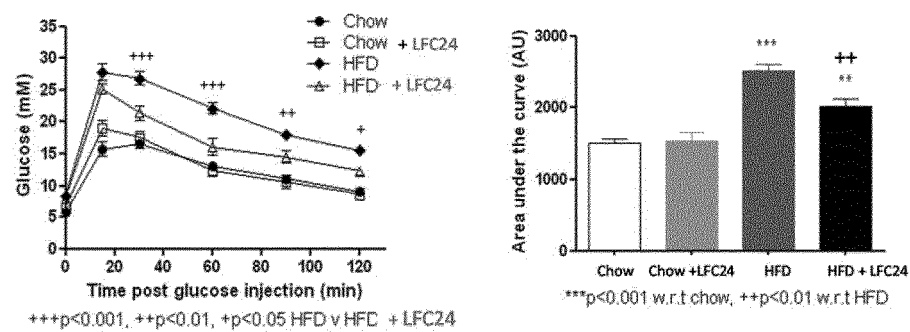

Using a diet induced obesity model animals were treated for 12 weeks with LFC 24. Treatment with LFC24 in the context of high fat feeding improved glucose clearance during a GTT compared to high fat feeding alone. LFC24 had no effect during chow feeding (FIG. 11). This improvement in glycaemic control can be explained by up-regulation of pAKT expression in adipose tissue (FIG. 12), skeletal muscle and liver (data not shown). pAKT is a key insulin signalling molecule that regulates glycaemic control.

Inflammation and Glycaemic Control

In the diet induced obesity model, LFC24 induced an anti-inflammatory effect wherein feeding a HFD with LFC24 prevented the pro-inflammatory, insulin de-sensitising effect of the HFD alone. LFC24 significantly reduced the secretion of TNFα, IL-1β, and IL-18 secreted from bone marrow macrophages (FIG. 13). Furthermore LFC24 significantly reduced ex vivo adipose tissue IL-6, IL-1β and TNFα secretion (FIG. 14).

Inflammation—Glycaemic Control Cross Talk

To define the specificity of the effect of LFC24 on the pro-inflammatory insulin se-sensitising axis we demonstrated that LFC24 can prevent the pro-inflammatory effect of IL-1β and TNFα by reducing IL-6 secretion from 3T3-L1 adipocytes and this was concomitant with an improvement of the insulin signalling molecules pAKT and glucose transporter GLUT4 (FIG. 15).

The invention is not limited to the embodiments hereinbefore described which may be varied in construction and detail without departing from the spirit of the invention.

The invention claimed is:

1. A method of improving glycemic management in a mammal in need thereof by increasing post-prandial insulin secretion or lowering blood plasma glucose levels, the method comprising administering to the mammal a peptide consisting of an amino acid sequence selected from the group consisting of SEQ ID NOs: 1-11.

2. A method of improving glycemic management in a mammal in need thereof by lowering liver fat content, reducing high fat diet or obesity induced inflammation, regulating glucose homeostasis in a mammal in need thereof, treating hyperglycemia, or attenuating insulin resistance in a mammal in need thereof, the method comprising administering to the mammal a peptide consisting of an amino acid sequence selected from the group consisting of SEQ ID NOs: 1-11.

* * * * *

SEQUENCE LISTING

<160> NUMBER OF SEQ ID NOS: 11

<210> SEQ ID NO 1
<211> LENGTH: 19
<212> TYPE: PRT
<213> ORGANISM: Artificial Sequence
<220> FEATURE:
<223> OTHER INFORMATION: Synthetic peptide

<400> SEQUENCE: 1

His Gln Pro His Gln Pro Leu Pro Pro Thr Val Met Phe Pro Pro Gln
1               5                   10                  15

Ser Val Leu

<210> SEQ ID NO 2
<211> LENGTH: 25
<212> TYPE: PRT
<213> ORGANISM: Artificial Sequence
<220> FEATURE:
<223> OTHER INFORMATION: Synthetic peptide

<400> SEQUENCE: 2

His Gln Pro His Gln Pro Leu Pro Pro Thr Val Met Phe Pro Pro Gln
1               5                   10                  15

Ser Val Leu Ser Leu Ser Gln Ser Lys
            20                  25

<210> SEQ ID NO 3
<211> LENGTH: 24
<212> TYPE: PRT
<213> ORGANISM: Artificial Sequence
<220> FEATURE:
<223> OTHER INFORMATION: Synthetic peptide

<400> SEQUENCE: 3

Leu Gln Ser Trp Met His Gln Pro His Gln Pro Leu Pro Pro Thr Val
1               5                   10                  15

Met Phe Pro Pro Gln Ser Val Leu
            20

<210> SEQ ID NO 4
<211> LENGTH: 30
<212> TYPE: PRT
<213> ORGANISM: Artificial Sequence
<220> FEATURE:
<223> OTHER INFORMATION: Synthetic peptide

<400> SEQUENCE: 4

Leu Gln Ser Trp Met His Gln Pro His Gln Pro Leu Pro Pro Thr Val
1               5                   10                  15

Met Phe Pro Pro Gln Ser Val Leu Ser Leu Ser Gln Ser Lys
            20                  25                  30

<210> SEQ ID NO 5
<211> LENGTH: 12
<212> TYPE: PRT
<213> ORGANISM: Artificial Sequence
<220> FEATURE:
<223> OTHER INFORMATION: Synthetic peptide

<400> SEQUENCE: 5

Pro Pro Gln Ser Val Leu Ser Leu Ser Gln Ser Lys
1               5                   10

<210> SEQ ID NO 6
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 6

Met His Gln Pro His Gln Pro Leu Pro Pro Thr Val Met Phe Pro Pro
1               5                   10                  15

Gln Ser Val Leu
        20

<210> SEQ ID NO 7
<211> LENGTH: 26
<212> TYPE: PRT
<213> ORGANISM: Artificial Sequence
<220> FEATURE:
<223> OTHER INFORMATION: Synthetic Sequence

<400> SEQUENCE: 7

Met His Gln Pro His Gln Pro Leu Pro Pro Thr Val Met Phe Pro Pro
1               5                   10                  15

Gln Ser Val Leu Ser Leu Ser Gln Ser Lys
        20                  25

<210> SEQ ID NO 8
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 8

Ser Trp Met His Gln Pro His Gln Pro Leu Pro Pro Thr Val Met Phe
1               5                   10                  15

Pro Pro Gln Ser Val Leu
        20

<210> SEQ ID NO 9
<211> LENGTH: 28
<212> TYPE: PRT
<213> ORGANISM: Artificial Sequence
<220> FEATURE:
<223> OTHER INFORMATION: Synthetic peptide

<400> SEQUENCE: 9

Ser Trp Met His Gln Pro His Gln Pro Leu Pro Pro Thr Val Met Phe
1               5                   10                  15

Pro Pro Gln Ser Val Leu Ser Leu Ser Gln Ser Lys
        20                  25

<210> SEQ ID NO 10
<211> LENGTH: 50
<212> TYPE: PRT
<213> ORGANISM: Artificial Sequence
<220> FEATURE:
<223> OTHER INFORMATION: Synthetic peptide

<400> SEQUENCE: 10

Tyr Pro Val Glu Pro Phe Thr Glu Ser Gln Ser Leu Thr Leu Thr Asp
1               5                   10                  15

Val Glu Asn Leu His Leu Pro Leu Pro Leu Leu Gln Ser Trp Met His
        20                  25                  30

Gln Pro His Gln Pro Leu Pro Pro Thr Val Met Phe Pro Pro Gln Ser
            35                  40                  45

Val Leu
    50

<210> SEQ ID NO 11
<211> LENGTH: 56

```
<212> TYPE: PRT
<213> ORGANISM: Artificial Sequence
<220> FEATURE:
<223> OTHER INFORMATION: Synthetic peptide

<400> SEQUENCE: 11

Tyr Pro Val Glu Pro Phe Thr Glu Ser Gln Ser Leu Thr Leu Thr Asp
 1               5                  10                  15

Val Glu Asn Leu His Leu Pro Leu Pro Leu Leu Gln Ser Trp Met His
            20                  25                  30

Gln Pro His Gln Pro Leu Pro Pro Thr Val Met Phe Pro Pro Gln Ser
        35                  40                  45

Val Leu Ser Leu Ser Gln Ser Lys
50                  55
```